United States Patent
Herzinger et al.

(10) Patent No.: US 7,151,605 B1
(45) Date of Patent: Dec. 19, 2006

(54) METHODOLOGY FOR PROVIDING GOOD DATA AT ALL WAVELENGTHS OVER A SPECTROSCOPIC RANGE

(75) Inventors: Craig M. Herzinger, Lincoln, NE (US); Steven E. Green, Lincoln, NE (US); Ronald A. Synowicki, Lincoln, NE (US); James D. Welch, Omaha, NE (US)

(73) Assignee: J.A. Woollam Co., Inc, Lincoln, NE (US)

( * ) Notice: Subject to any disclaimer, the term of this patent is extended or adjusted under 35 U.S.C. 154(b) by 54 days.

(21) Appl. No.: 11/009,489

(22) Filed: Dec. 11, 2004

Related U.S. Application Data

(63) Continuation-in-part of application No. 09/862,881, filed on Aug. 9, 2001, now Pat. No. 6,831,740.

(60) Provisional application No. 60/207,170, filed on May 26, 2000.

(51) Int. Cl.
*G01J 4/00* (2006.01)

(52) U.S. Cl. .................................................. 356/369

(58) Field of Classification Search ................ 356/319, 356/300–334, 400–425, 364–369
See application file for complete search history.

(56) References Cited

U.S. PATENT DOCUMENTS

| | | | |
|---|---|---|---|
| 3,579,105 A | 5/1971 | Scott | 324/99 |
| 3,734,621 A * | 5/1973 | Moody et al. | 356/325 |
| 3,790,798 A | 2/1974 | Sternberg et al. | 250/345 |
| 3,888,569 A * | 6/1975 | Munnerly et al. | 351/211 |
| 3,986,776 A | 10/1976 | George | 356/88 |
| 4,079,256 A | 3/1978 | Ford et al. | 250/343 |
| 4,084,248 A | 4/1978 | Scott | 364/571 |
| 4,455,097 A | 6/1984 | Ichikawa et al. | 356/323 |
| 4,577,106 A | 3/1986 | Fukasawa et al. | 250/347 |
| 4,672,192 A * | 6/1987 | Muka et al. | 250/205 |
| 4,832,491 A | 5/1989 | Sharpe et al. | 356/326 |
| 5,872,630 A * | 2/1999 | Johs et al. | 356/369 |
| 5,936,734 A * | 8/1999 | Johs et al. | 356/364 |
| 5,991,022 A | 11/1999 | Buermann et al. | 356/319 |
| 6,510,725 B1 * | 1/2003 | Zhang et al. | 73/1.79 |
| 2004/0131353 A1 * | 7/2004 | Cannon et al. | 398/1 |

* cited by examiner

*Primary Examiner*—Gregory J. Toatley, Jr.
*Assistant Examiner*—Isiaka O. Akanbi
(74) *Attorney, Agent, or Firm*—James D. Welch

(57) ABSTRACT

Disclosed is methodology for obtaining data of improved precision, including detection and replacement of data determined to be suspect to provide good data over a spectroscopic range of wavelengths.

10 Claims, 3 Drawing Sheets

METHODOLOGY FOR PROVIDING GOOD DATA AT ALL WAVELENGTHS OVER A SPECTROSCOPIC RANGE

This Application is a CIP Allowed Utility application Ser. No. 09/862,881 Filed Aug. 9, 2001, (U.S. Pat. No. 6,831,740 as of Dec. 14, 2004), and Claims Benefit of Provisional Application Ser. No. 60/207,170, Filed May 26, 2000.

TECHNICAL FIELD

The present invention relates to the use of electromagnetic radiation to investigate sample systems, and more particularly to methodology for simplifying the acquiring a good set of spectroscopic data, comprising replacement of data determined to be suspect at one or more wavelengths with reacquired data at said at one or more wavelengths, instead of reacquiring data over said entire spectroscopic range of wavelengths.

BACKGROUND

Spectrophotometer systems enable investigation of sample systems with multiple wavelengths of electromagnetic radiation. Ellipsometer, polarimeter or the like systems also enable investigation of sample systems with multiple wavelengths of electromagnetic radiation, but in adition provide insight to phase shifts entered between orthogonal components of a polarized beam of electromagnetic radiataion by interaction with a sample.

Two basically distinguishable Spectrophotometer system configurations are possible. The first comprises a spectroscopic source of electromagnetic radiation and a single detector which, in use, are applied sequentially to provide base-line and sample data at different times. The second configuration again comprises a spectroscopic source of electromagnetic radiation, but further provides a beam-splitter means to provide two beams of electromagnetic radiation, which two beams are simultaneoulsy applied to provide base-line and sample data, said base-line and sample data generation being mediated via two separate detectors. In either case said systems can include a monochrometer to allow selecting or scanning through wavelengths, or can provide multi-element detector(s) which simultaneously monitors a plurality of wavelengths.

Continuing, conventional dual, (in space), electromagnetic beam Spectrophotometer systems allow simultaneous monitoring of baseline reference, and sample system investigation intensities via different beams of electromagnetic radiation, hence, allow immediate comparison of sample to baseline data on a wavelength by wavelength basis. It is noted that the two beams are generally derived from a single spectroscopic source of electromagnetic radiation and are produced by a beam-splitter means. The simultaneous availability of baseline and sample system data enables forming the desired result of an output ratio of the sample system investigation intensity signal with the corresponding baseline reference intensity signal. Said methodology can be practiced whether data is sequentially acquired by a scan of wavelengths or a multiplicity of wavelengths is simultaneously investigated depending on, for instance, if a monochrometer and single detector, or wavelength separating means, (eg. dispersive element or a plurality of laterally disposed filter etc. means), and multiple detector elements in the two detectors that intercept the two separated beams, are present, respectively. It is further noted that as the two electromagnetic beams typically have a single spectroscopic source of electromagnetic radiation, source electromagnetic intensity drift and noise etc. show-up equally in real-time in baseline reference and sample system investigation signals, and that causes ratios of sample system investigation intensity, to the reference baseline intensity signals, at all wavelenghts, to be compensated therefore. However, as two Detectors are involved, (one to intercept the beam which interacts with a sample and one to intercept the beam that does not), it should be recognized that errors attributable to the Detectors, (eg. different calibration drifting characteristics), is not automatically compensated.

It should then be appreciated that while simultaneous use of two beams derived from a single spectroscopic source of electromagnetic radiation facilitates automatic compensation of changes in the output of said spectroscopic source of electromagnetic radiation, said approach also requires that two Detectors be utilized, and errors can develop based on changes in the two Detectors which do not necessarily exactly "track" one another. In comparison, it should also be appreciated that use of a single beam and single detector element to sequentially provide base-line and sample system investigation data, while avoiding the problems associated with the presence of two detectors, predisposes data acquired by use thereof to error caused by the requirement that electromagnetic radiation used to provide base-line and sample investigation data, while from the same source, must be accessed at different times, thus sorce output characteristic drift becomes a source of problems.

Continuing, typical practice, when investigating a sample system with a spectrophotometer using a single source beam and single detector, (dual beam in time), is to do baseline reference intensity data acquisition, wherein multiple wavelengths are dispersed, or perhaps separated by filtering etc., and monitored simultaneously by multiple detector elements, or wherein monochrometer is used to scan through a range of wavelengths and single detector element is utilized to sequentially monitor the results. A sample system is then entered into the single electromagnetic beam spectrophotometer system and corresponding intensity data is similarly acquired. Comparison of the baseline reference results to the corresponding sample system present data, on a wavelength by wavelength basis, allows forming desired ratio results.

It is generally noted that it is relatively easy to set a spectrophotometer system in a baseline reference configuration and do a monochrometer scan of wavelengths, then set the spectrophotometer in a sample system present configuration and do a similar monochrometer scan of wavelengths. The present inventors however, have noted that said just described monochrometer scanning practice is less than optimum as monochrometers have finite wavelength repeatable selection precisions associated therewith. For instance, what a monochrometer passes as a wavelength of "X" in the baseline scan is not necessarily repeatably precisely the same as the wavelength identified as "X" passed during the sample system investigation scan. This lack of repeatability is complicated where actual value accuracy errors in wavelength selection occur. In addition, as mentioned, electromagnetic radiation source intensity fluctuations can occur during one, (ie. baseline or sample system investigation), scan which are not similar to those in another scan. And, it is again mentioned that even where two beams derived from a single source are simultaneoulsy utilized, two detectors must be applied, and said characteritic output from each of said two detectors can drift differently with time, thereby entering error.

Ellipsometer, polarimeter or the like systems comprise a Source of Electromagnetic radiation, (preferebly scpectroscopic), a Polarizer, optionally a Compensator, a Stage for supporting a sample, optionally a Compensator, an Analyzer and a Detector. It is also possible to include a Monochromator to enable scanning through a range of wavelengths. Data which can be obtained with Ellipsometers, Polarimeter or the like systems are a ratio of intensities of, and a phase angle between, orthogonal components of a polarized beam of electromagentic radiation caused by interaction with a sample.

With the present invention in mind, a Search of Patents was conducted. Perhaps the most relevant Patent found was U.S. Pat. No. 4,832,491 to Sharpe et al. Said Patent describes a method of using electromagnetic radiation to investigate a sample system, involving using a monochrometer to set a wavelength, obtaining reference data, obtaining sample system data, forming a ratio of the sample system and reference data, and repeating said steps for additional wavelengths. Another Patent, U.S. Pat. No. 3,790,798 to Sternberg et al., describes a single beam system wherein reference data is obtained with filters in place in said system which pass wavelengths other than those which are absorbed by a sample analyte, (eg. gas in a sample containing cell). Said 798 Patent describes obtaining both sample and reference data and forming a ratio therebetween.

A Patent to Fukasawa et al., U.S. Pat. No. 4,577,106, describes a double beam spectrophotometer which contains means for allowing acquisition of dark, reference, sample and reference data, in that order.

A Patent to George, U.S. Pat. No. 3,986,776 describes baseline compensation in a dual beam spectrophotometer. During a calibration run a baseline error signal is generated, and said error signal is used to adjust a ratio of a sample to baseline signal during sample data acquisition.

U.S. Pat. No. 4,079,256 to Ford et al., describes a double-beam system in which two evaluations are combined to produce a derived reference signal in a situation wherein sample and reference signals do not occur at the same time, because a single spectrophotometer detector system it utilized.

U.S. Pat. Nos. 4,084,248 and 3,579,105 to Scott describe dual beam systems in which in the calibration run two beams are compared at each wavelength and adjustment disparities are calculated, said adjustments being applied during sample runs.

Patents found by the Examiner during Prosecution of the Parent application Ser. No. 09/862,881 are:
 U.S. Pat. No. 5,991,022 to Buermann et al; and
 U.S. Pat. No. 4,455,097 to Ichikawa et al.

There are literally thousands of references available which focus on Ellipsometry, but none are known to teach partial replacement of spectroscopic data sets, hence none are identifed.

The focus of the presently disclosed invention is to teach partial substitution of data at specific wavelengths in a spectroscopic data set, said replaced data having been, by any means, determined to be suspect as to precision and/or accuracy.

Even in view of said prior art, need remains for, in the context of spectrophotometer and ellipsometer or the like systems, a methodology for improving the quality of data provided thereby.

DISCLOSURE OF THE INVENTION

In general, the present invention teaches methodology which enables obtaining better precision in Spectroscopic data acquired from application of electromagnetic beams to sample systems in Spectrophotometer and Ellipsometer, and Polarimeter or the like Systems. For general insight it is noted that the terminology "Precision" refers to the repeatability of data acquisition. This is in contrast to the meaning of the terminology "Accuracy", which refers to the determination of the actual value of a parameter. That is, acquired data can be very repeatable, (precise), but offset from an actual parameter value, (inaccurate). Ideally, of course, data should be both precise and accurate, but it is disclosed that the present invention is focused primarily on improving precision of data at all wavelengths over a wavelength range.

In the following there are presented specific examples of how the present invention can be practiced, some of which were originally presented in Parent application Ser. No. 09/862,881.

Single Beam Methodology

Proceeding, one approach to obtaining data utilizing a spectrophotometer system and which is relevant to the present invention, provides that a wavelength, (identified as "X"), in an electromagnetic beam from a spectroscopic source be passed by a monochrometer, and without change of said monochromater setting, sequential acquisition of both baseline reference and sample system present intensity data be conducted. That is both baseline-reference and sample system-present intensity data are acquired without changing the monochrometer setting. Said procedure is then repeated at each desired wavelength. While said approach eliminates the problems associated with monochrometer repeatability precision, in providing the same wavelength "X" each time a monochrometer is intended to be similarly set, said procedure can be time consuming. And, it is noted that this approach does not remove noise which can enter because, for instance, the reference and sample system intensity data are obtained at different times when the source of electromagnetic radiation might provide different intensity as a result of unavoidable fluctuations.

A generally representative present invention method of improving the precision of acquired intensity ratio data, where a single beam is utilized, comprises the steps of:

a. causing at least one wavelength in an electromagnetic beam to enter a detector, to the end that said detector produces a representative intensity signal;

b. causing said at least one wavelength in said electromagnetic beam to interact with a sample system and enter a detector, to the end that said detector produces a representative intensity signal;

c. causing said at least one wavelength in said electromagnetic beam to enter a detector, to the end that said detector produces a representative intensity signal;

d. forming a ratio of the intensities provided in steps a and c and if it is not within a selected acceptable range of deviation from 1.0, repeating steps a, b and c until a data set is achieved which provides a ratio formed between the intensities provided in steps a and c is within a selected acceptable range of deviation from, 1.0;

e. with a data set achieved which provides that a ratio formed between the intensities provided in steps a and c is within a selected acceptable range of deviation from, 1.0, forming a ratio between the intensity provided in step b and that provided by step a or step c or a composite of said intensities provided in steps a and c.

Another embodiment of improving the precision of acquired intensity ratio data comprises the steps of:

a. providing a spectrophotometer system including a spectroscopic source of a beam of electromagnetic radiation and monochrometer for allowing selecting of or scanning a range of wavelengths, a means for supporting a sample system, and a detector system; said spectophotometer system being configurable such that a produced beam of electromagnetic radiation is caused to interact with said sample system and enter said detector system;

b. performing steps b1, b2, and b3:

b1. causing said monochrometer to scan a selected range of wavelengths while obtaining a first baseline reference intensity data set;

b2. causing said monochrometer to scan said selected range of wavelengths while obtaining a sample system investigation intensity data set;

b3. causing said monochrometer to scan said selected range of wavelengths while obtaining a second baseline reference intensity data set; and c. at selected wavelength(s) whereat the ratio in said baseline reference intensity values obtained in steps b1 and b3 is within some selected range substantially near 1.0, utilizing baseline reference intensity data obtained in step b1 or b3 or a composite value of the step b1 and b3 baseline reference intensity data, to form a ratio with said sample system investigation intensity data obtained in b2; and d. identifying a wavelength at which the ratio of said baseline reference intensity values obtained in steps b1 and b3 is not within said selected range substantially near 1.0, and setting said monochrometer to pass said identified wavelength; then without changing said monochrometer setting obtaining:

d1. first baseline reference intensity data;

d2. sample system investigation intensity data;

d3. second baseline reference intensity data; and e. utilizing first and second baseline reference intensity data obtained in step d1. or d3 or a composite value of the baseline reference intensity data obtained in step d1 and d3, and using said baseline reference intensity data obtained in step d1 or d3 or a composite value thereeof to form a ratio with said sample system investigation intensity data obtained in d2 at wavelengths whereat the ratio in said intensity values obtained in steps d1 and d3 is within some selected range substantially near 1.0;

f. optionally repeating steps d and e for additional wavelength(s) at which the ratio in said intensity values obtained in steps b1 and b3 is not within said selected range substantially near 1.0.

A modified approach to obtaining data utilizing a spectrophotometer system and which is relevant to the present invention, involves performing a first baseline reference intensity data acquisition either at a single wavelength or over a range of wavelengths, then doing a similar procedure with a sample system in place, and then doing a second baseline reference intensity data acquisition either at a single wavelength or over a range of wavelengths. If there is a significant deviation from 1.0 in a ratio between the first and second baseline reference data acquisition at any wavelength then a composite, (eg. an average), value of the first and second baseline reference data results is used as the baseline reference value in forming a ratio with the sample system investigation intensity data. If the ratio of data acquired in both baselines, however, is within some tolerable deviation from 1.0, either of the baseline data values, or a composite thereof, can be used to form a desired ratio with corresponding sample data. While this methodology might not be absolutely novel in view of prior art, it is believed that where it is practiced with a Spectrophotometer System which causes a beam of electromagnetic radiation to approach a sample at an oblique angle to a reference surface thereof, it is novel.

Note, in addition, in the just described method, where the value of the first and second baseline reference data differ significantly at a wavelength, said baseline and sample present data can be reacquired, and the original data replaced with new sample and associated with baseline results. It is believed that said step of replacing data from which a sample to baseline ratio is formed is definitely distinguishing and Patentable over the prior art.

Another expression of present invention methodology provides for performing a first baseline reference intensity scan over a range of wavelengths, then performing a similar scan with a sample system in position to enable achieving a sample system present intensity data set, and then performing a second baseline reference intensity scan over said range of wavelengths. Then, if the first and second baseline reference intensity scans over said range of wavelengths provide intensity data which significantly differ at any wavelength, a monochrometer is caused to provide said wavelength, and the intensity data is retaken for both baseline reference and sample system present, without changing the monochrometer setting. That is, if there is evidence that, in a scan over a range of wavelengths, the baseline changed after a first baseline reference data acquisition was performed and before or during acquiring data with a sample system in place, then data is reacquired at just the wavelength(s) whereat a baseline change is indicated by a ratio with a second baseline reference intensity data differing from 1.0 by some significant amount, (note that throughout all examples in this Specification what is "significant" should be considered to vary from one data collection procedure to another, and is user determinable). The second set of baseline reference intensity data is taken after intensity data is acquired from said sample system. Possibly erroneous Intensity data at all said identified wavelength(s) is, at each wavelength, typically re-acquired for two baseline references, one before and one after the sample system present case, and for the sample system present case, again without changing the monochrometer setting. It should be appreciated that this embodiment enables achieving very precise data at all wavelengths, without the need to reconfigure the spectrophotometer system for baseline reference and sample system-present cases at every wavelength utilized and for which good data was already achieved, (which reconfiguration procedure, as mentioned, even if computerized, can be time consuming). Once acceptable data is indicated, a ratio can be formed by dividing the sample system data with either of the baseline data values, or more typically with a composite formed therefrom. (Note that if the two baselines are equal, said composite will typically be of the same value as the baseline values. That is a composite is typically, though not necessarily, an averaged baseline value).

A variation on the just described present invention methodology provides that where a plurality of wavelengths are identified wherein a ratio of the first and second baselines deviates unacceptably from 1.0, then new first baseline, sample present, and second baseline data are scanned, or perhaps simultaneously obtained, (eg. by two detector elements), at at least two of said wavelengths. Said new data can then be applied to replace the original data at at least some of said identified wavelengths, if said new data provides that a ratio of the new first and second baselines does not unacceptably deviate from 1.0.

Continuing, it is generally noted that a common source of variation of repeatability precision in monochrometer wavelength selection is based on the presence of peaks in electromagnetic source intensity spectra. Where a monochrometer is required to select an intensity at a wavelength which is in a range of wavelengths in which intensity changes quickly over a small range of wavelengths it is very likely that repeated settings of the monochrometer at an intended specific wavelength will result in different intensity values being provided. Where intensity is relatively constant as a function of wavelength, this sensitivity of course is far less a problem. Another source of intensity variation is based in purge related change of atmospheric conditions between a source and detector of a beam of electromagnetic radiation. Other sources of error include that due to random noise, but it is noted that random noise can be averaged-out by obtaining data over longer periods.

A modified method of improving the precision of acquired intensity ratio data comprises the steps of:

a. providing a spectrophotometer system including a spectroscopic source of a beam of electromagnetic radiation and monochrometer for allowing selecting of or scanning a range of wavelengths, a means for supporting a sample system, and a detector system; said spectophotometer system being configurable such that a produced beam of electromagnetic radiation is caused to interact with said sample system and enter said detector system;

b. performing steps b1 b2, and b3:

b1. causing said monochrometer to scan a selected range of wavelengths while obtaining a first baseline reference intensity data set;

b2. causing said monochrometer to scan said selected range of wavelengths while obtaining sample system investigation intensity data set;

b3. causing said monochrometer to scan said selected range of wavelengths while obtaining a second baseline reference intensity data set; and c. at selected wavelength(s) whereat the ratio in said baseline reference intensity values obtained in steps b1 and b3 is within some selected range substantially near 1.0, utilizing baseline reference intensity data obtained in step b1 or b3, or a composite value of the baseline reference intensity data obtained in steps b1 and b3 as baseline reference intensity data, to form a ratio with said sample system investigation intensity data obtained in b2; and d. identifying a plurality of wavelengths at which the ratio in said baseline reference intensity values obtained in steps b1 and b3 is not within said selected range substantially near 1.0, and for each of at least two thereof:

d1. causing said monochrometer to scan said at least two of said plurality of identified wavelengths while obtaining a first baseline reference intensity data set;

d2. causing said monochrometer to scan said at least two of said plurality of identified wavelengths while obtaining a sample system investigation intensity data set;

d3. causing said monochrometer to scan said at least two of said plurality of identified wavelengths while obtaining a second baseline reference intensity data set;

e. for at least one of said at least two wavelengths utilizing first or second baseline reference intensity data obtained in step d1 or d3, or a composite value of the baseline reference intensity data obtained in steps d1 and d3 as a baseline reference intensity data, to form a ratio with said sample system investigation intensity data obtained in d2.

Another modified method of improving the precision of acquired intensity ratio data comprises the steps of:

a. providing a spectrophotometer system including a spectroscopic source of a beam of electromagnetic radiation, a means for supporting a sample system, and a detector system; said spectophotometer system being configurable such that a produced beam of electromagnetic radiation is caused to interact with said sample system and enter said detector system;

b. for each of a plurality of wavelengths obtaining, in any functional order, intensity data corresponding to:

b1. a first baseline reference intensity data;

b2. sample system investigation intensity data;

b3. a second baseline reference intensity data; and c. repeating said step b. to reacquire all data if at any selected wavelength(s) the ratio between the first and second baseline reference intensity data acquired in steps b1 and b3 is not within a selected range substantially near 1.0; and d. with an acceptable set of intensity data secured, at selected wavelength(s) utilizing said baseline reference intensity data obtained in step b1 or b3 or a composite value of the baseline intensity values obtained in steps b1 and b3, forming a ratio with said sample system investigation intensity data obtained in step b2.

Another modified method yet of improving the precision of acquired intensity ratio data comprises the steps of:

a. providing a spectrophotometer system including a spectroscopic source of a beam of electromagnetic radiation, a means for supporting a sample system, and a multiple element detector system; said spectophotometer system being configurable such that a produced beam of electromagnetic radiation is caused to interact with said sample system and enter said multiple element detector system;

b. for each of a plurality of wavelengths simultaneously obtaining, in any functional order, intensity data corresponding to:

b1. a first baseline reference intensity data;

b2. sample system investigation intensity data;

b3. a second baseline reference intensity data; and c. repeating said step b. to reacquire all data if at any selected wavelength(s) the ratio between the first and second baseline reference intensity data acquired in steps b1 and b3 is not within a selected range substantially near 1.0; and d. with an acceptable set of intensity data simultaneously secured, at selected wavelength(s) utilizing said baseline reference intensity data obtained in step b1 or b3 or a composite value of the baseline intensity values obtained in steps b1 and b3, to form a ratio with said sample system investigation intensity data obtained in step b2.

Yet another modified method of improving the precision of acquired intensity ratio data comprises the steps of:

a. providing a spectrophotometer system including a spectroscopic source of a beam of electromagnetic radiation, a means for supporting a sample system, and a detector system; said spectophotometer system being configurable such that a produced beam of electromagnetic radiation is caused to interact with said sample system and enter said detector system;

b. for each of a plurality of wavelengths obtaining, in any functional order, intensity data corresponding to:

b1. first baseline reference intensity data;

b2. sample system investigation intensity data;

b3. second baseline reference intensity data; and c. at selected wavelength(s) utilizing said baseline reference intensity data obtained in step b1. or b3. or a composite value formed said baseline intensity data obtained in steps b1 and b3, to form a ratio with said sample system investigation intensity data obtained in step b2 if a ratio between the first and second baseline reference intensity data acquired in steps b1 and b3 is within a selected range which is in a range substantially near 1.0; and d. identifying at least one selected wavelength(s) whereat the ratio between the first and second baseline reference intensity data acquired in steps b1 and b3 is not within a selected range substantially near 1.0, reacquiring baseline reference intensity data and sample system investigation intensity data and utilizing said reacquired baseline reference intensity data in forming a ratio with said reacquired sample system investigation intensity data.

A further modification of the present invention method of acquiring precise spectrophotometer intensity ratio data comprises the steps of:

a. providing a spectrophotometer system including a spectroscopic source of a beam of electromagnetic radiation, a means for supporting a sample system, and a multiple element detector system; said spectophotometer system being configurable such that a produced beam of electromagnetic radiation is caused to interact with said sample system and enter said multiple element detector system;

b. for each of a plurality of wavelengths simultaneously obtaining, in any functional order, intensity data corresponding to:

b1. first baseline reference intensity data;
b2. sample system investigation intensity data;
b3. second baseline reference intensity data; and c. at selected wavelength(s) utilizing said baseline reference intensity data obtained in step b1 or b3 or a composite value of the baseline reference intensity values obtained in steps b1 and b3, to form a ratio with said sample system investigation intensity data obtained in step b2 if a ratio between the first and second baseline reference intensity data acquired in steps b1 and b3 is within a selected range which is in a range substantially near 1.0; and d. reacquiring baseline reference intensity data and sample system investigation intensity data at at least one selected wavelength(s) whereat the ratio between the first and second baseline reference intensity data acquired in steps b1 and b3 is not within a selected range substantially near 1.0, and utilizing said reacquired baseline reference intensity data in forming a ratio with said reacquired sample system investigation intensity data.

Two Beam Methodology

A general method of improving the precision of acquired intensity ratio data where two beams are formed and utilized, comprises the steps of:

a. providing a beam of electromagnetism comprising at least one wavelength and causing it to be divided into first and second electromagnetic beams by a beam splitting means;

b. causing at least one wavelength in said first electromagnetic beam to enter a detector, to the end that said detector produces a representative intensity signal;

c. in either order practicing the following steps:

c1. causing said at least one wavelength in said second electromagnetic beam to enter a detector, to the end that said detector produces a representative intensity signal;

c2. causing said at least one wavelength in said second electromagnetic beam to interact with a sample system and enter a detector, to the end that said detector produces a representative intensity signal;

one of said steps c1 and c2 optionally being performed simultaneously with step b.;

d. forming a ratio of the intensities provided in steps b and c1 and if it is not within a selected acceptable range of deviation from a determined expected value, repeating steps b and c until a data set is achieved which provides a ratio formed between the intensities provided in steps b and c1 is within a selected acceptable range of deviation from said determined expected value;

e. with a data set achieved which provides that a ratio formed between the intensities provided in steps b and c1 is within a selected acceptable range of deviation from said determined expected value, forming a ratio between the intensity provided in step c2 and that provided by step b or step c1 or a composite of said intensities provided in steps b and c1.

A prefered two beam method of improving the precision of acquired intensity ratio data comprises the steps of:

a. providing beam of electromagnetism and causing it to be divided into first and second electromagnetic beams by a beam splitting means;

b. causing at least one wavelength in said first electromagnetic beam to enter a first detector without first interacting with a sample system, to the end that said first detector produces a representative intensity signal;

c1. simultaneously with step b causing said at least one wavelength in said second electromagnetic beam to enter a second detector without first interacting with a sample system, to the end that said second detector produces a representative intensity signal;

performing steps b and c2 in either order:

c2. causing said at least one wavelength in said second electromagnetic beam to interact with a sample system and enter the same detector used in step c1 to the end that said detector produces a representative intensity signal;

d. forming a ratio of the intensities provided in steps b and c1 and if it is not within a selected acceptable range of deviation from a determined expected value applying a calibration factor to intensity data obtained from the detector used in step b and/or c1;

e. with any calibration factor to intensity data applied, with a data set achieved which provides that a ratio formed between the intensities provided in steps b and c1 is within a selected acceptable range of deviation from a determined expected value, forming a ratio between the intensity provided in step c2 and that provided by step b or step c1 or a composite of said intensities provided in steps b and c1;

to the end that intensity ratio data is acquired;

said method then further involving performing steps f1, f2 and f3, said steps f1, f2 and f3 being:

f1. causing at least one wavelength in said first electromagnetic beam to enter said first detector without first interacting with a sample system, to the end that said first detector produces a representative intensity signal;

f2. simultaneous with step f1 causing said at least one wavelength in said second electromagnetic beam to enter said second detector without first interacting with a sample system, to the end that said second detector produces a representative intensity signal;

f3. forming a ratio of the intensities provided in steps f1 and f2 and if it is not within a selected acceptable range of deviation from a determined expected value, repeating steps a–e.

Yet another two beam present method of improving the precision of acquired intensity ratio data then comprises the steps of:

a. providing a spectrophotometer system including a spectroscopic source of a beam of spectroscopic electromagnetic radiation, a beam splitter means, a means for providing a sample system and first and second multi-element detector systems; said spectophotometer system being configurable such that a produced beam of electromagnetic radiation is caused be split into two beams by said beam splitter means, one of said two beams being caused to either enter directly into said first multi-element detector or interact with a sample system and then enter said first multi-element detector system; and the other of said two beams being caused to enter directly into said second multi-element detector;

b. for a plurality of wavelengths simultaneously obtaining:

b1. baseline reference intensity data from said second multi-element detector; and b2. obtaining, in either order, intensity data from said first multi-element detector both with a sample system present and with the sample system removed; (note it is functionally preferred to simultaneously obtain baseline reference data from both first and second detectors);

c. at at least some wavelengths forming a ratio between the baseline intensity data obtained in step b1, and the intensity data obtained in step b2 which was obtained with the sample system removed.

If, for a wavelength, a ratio between said baseline reference intensity data is within a selected range substantially near a determined expected value, using the baseline intensity data obtained in step b1, or the intensity data obtained in step b2 which was obtained with the sample system removed, or a composite formed from the baseline intensity data obtained in step b1 and the intensity data obtained in step b2 which was obtained with the sample system removed, to form a ratio with the intensity data obtained in step b2 which was obtained with the sample system present.

However, if, for a wavelength, a ratio between the baseline intensity data obtained in step b1, and the intensity data obtained in step b2 which was obtained with the sample system removed is not within a selected range substantially near a determined expected value, then performing a selection from the group consisting of:

repeating steps b and c; and applying a correction factor to the intensity data obtained from said second and/or first detector with the sample system removed in steps b1 and b2 respectively;

to the end that the ratio between the baseline intensity data obtained in step b1, and the intensity data obtained in step b2 which was obtained with the sample system removed is within a selected range substantially near a determined expected value;

and then with any correction factor to the intensity data obtained from said second and/or first detector applied, forming a ratio between resulting intensity data related to step b2 from said first detector obtained with a sample system present to the baseline intensity data obtained in step b1, or the intensity data obtained in step b2 which was obtained with the sample system removed, or a composite of the baseline intensity data obtained in step b1 and the intensity data obtained in step b2 which was obtained with the sample system removed, with any required calibration factor being applied to the intensity data obtained from said second or first detector with the sample system removed in steps b1 and b2;

to the end that intensity ratio data is acquired;

To assure that neither detector changed during the above recited procedure, said just recited method preferably further comprises steps d1, d2 and d3, wherein said steps d1, d2 and d3 are:

d1. causing at least one wavelength in said first electromagnetic beam to enter said first detector without first interacting with a sample system, to the end that said first detector produces a representative intensity signal;

d1. simultaneous with step d1 causing said at least one wavelength in said second electromagnetic beam to enter said second detector without first interacting with a sample system, to the end that said second detector produces a representative intensity signal;

d3. at said at least one wavelength forming a ratio of the intensities provided in steps d1 and d2 and if it is not within a selected acceptable range of deviation from a determined expected value repeating steps a–c for at least said at least one wavelength. Of course the repeating of steps a–c is optional and whether to practice it is at the discretion of a user.

Said just described method can, of course, be modified to provide that rather than working single wavelength by single wavelength, a plurality of wavelengths is scanned at each baseline and sample investigation step. And further, said just described method can be modified to provide that the monochromer is removed from the system and that each of the first and second Detectors comprise multiple detector elements. With a system so configured, multiple wavelengths can be simultaneously monitored at each step and the data acquired be analyzed to determine at which wavelengths the data is acceptable, (based on the ratio between the baseline intensity data obtained in step b1, and the intensity data obtained in step b2 which was obtained with the sample system removed being within an acceptable deviation range from a selected value for a wavelength). Further, as generally true in all embodiments of the present invention, said method can be practiced using a source of two beams that provides but a single wavelength as output.

Again, where baseline and sample data is available from investigation at multiple wavelengths, obtaining replacement data for wavelengths at which the baseline ratio is not within an acceptable range around a selected value can proceed on a wavelength by wavelength basis, or alternatively, a plurality of wavelengths can be identified at which data should be replaced and new baseline and sample data can be sequentially acquired, (via monochromer scanning where, for instance, the first and second detectors are of single detector element construction), or simultaneoulsy acquired, (where the first and second detectors each comprise a plurality of detector elements), for at least some of said wavelengths, prior to any analysis of the newly acquired data.

Oblique Angle of Incidence Methodology

As alluded to earlier herein, a further method of improving the precision of acquired intensity ratio data comprises the steps of:

a. providing a spectrophotometer system including a spectroscopic source of a beam of electromagnetic radiation and monochrometer for allowing selecting of wavelengths, a means for supporting a sample system and a detector system; said spectophotometer system being configurable such that a produced beam of electromagnetic radiation is caused to impinge upon a reference surface of a sample system placed on said means for supporting a sample system at an oblique angle thereto and enter said detector system;

b. setting said monochrometer to pass a selected wavelength; then without changing said monochrometer setting obtaining, in any functional order:
   b1. baseline reference intensity data; and
   b2. sample system investigation intensity data;

c. utilizing said baseline reference intensity data to form a ratio with said sample system investigation intensity data;

d. optionally repeating said steps b and c for different monochrometer settings.

It is noted that the determined expected value for the ratio between the two baselines is 1.0.

Another present invention method of acquiring precise spectrophotometer intensity ratio data, said method comprising the steps of:

a. providing a spectrophotometer system including a spectroscopic source of a beam of electromagnetic radiation and monochrometer for allowing selecting of wavelengths, a means for supporting a sample system and a detector system; said spectophotometer system being configurable such that a produced beam of electromagnetic radiation is caused to impinge upon a reference surface of a sample system placed on said means for supporting a sample system at an oblique angle thereto, and enter said detector system;

b. setting said monochrometer to pass a selected wavelength; then without changing said monochrometer setting obtaining, in any functional order:
   b1. a first baseline reference intensity data;
   b2. sample system investigation intensity data;
   b3. a second baseline reference intensity data; and c. utilizing said baseline reference intensity data obtained in step b1 or b3, or a composite value of the baseline reference intensity values obtained in steps b1 and b3, to form a ratio with said sample system investigation intensity data obtained in step b2.

d. optionally repeating said steps b and c for different monochrometer settings.

Another method of improving the precision of acquired intensity ratio data comprises the steps of:

a. providing a spectrophotometer system including a spectroscopic source of a beam of electromagnetic radiation and monochrometer for allowing selecting of wavelengths, a means for supporting a sample system and a multi-element detector system; said spectophotometer system being configurable such that a produced beam of electromagnetic radiation is caused to impinge upon a reference surface of a sample system placed on said means for supporting a sample system at an oblique angle thereto and enter said multi-element detector system;

b. for a plurality of wavelengths, simultaneously obtaining, in any functional order:
   b1. baseline reference intensity data; and
   b2. sample system investigation intensity data;

c. at at least one wavelength utilizing said baseline reference intensity data to form a ratio with corresponding sample system investigation intensity data;

d. optionally repeating said steps b and c for different wavelength(s).

Another method of acquiring precise spectrophotometer intensity ratio data comprises the steps of:

a. providing a spectrophotometer system including a spectroscopic source of a beam of electromagnetic radiation, a means for supporting a sample system and a multi-element detector system; said spectophotometer system being configurable such that a produced beam of electromagnetic radiation is caused to impinge upon a reference sample system placed on said means for supporting a sample system at an oblique angle thereto, and enter said multi-element detector system;

b. for a plurality of wavelengths, simultaneously obtaining, in any functional order:
   b1. a first baseline reference intensity data;
   b2. sample system investigation intensity data;
   b3. a second baseline reference intensity data; and c. at at least one wavelength utilizing said baseline reference intensity data obtained in step b1 or b3, or a composite value of the baseline reference intensity values obtained in steps b1 and b3, to form a ratio with corresponding said sample system investigation intensity data obtained in step b2.

d. optionally repeating said steps b and c for different wavelength(s).

General Method

A general method of facilitating production of a good spectroscopic data set comprising the steps of:

a) acquiring a spectroscopic data set which represents the effect a sample has on a beam of electromagnetic radiation over a plurality of wavelengths;

b) determining that data acquired in step a is not good at at least one, but not at all wavelengths;

c) reacquiring data at said at least one wavelength and replacing the originally obtained data with said reacquired data, such that the necessity of reacquiring an entirely new data set is avoided.

The spectroscopic data set can be acquired one wavelength at a time, utilizing a monochromator to scan through said wavelengths, or a plurality of wavelengths can be detected simultaneously. The collected data can represent the effect a sample has on reflected or transmitted intensity, or on reflected or transmitted or reflected ellipsometric PSI or ellipsometric DELTA.

General Discussion

It should be appreciated then that the present invention can, in various embodiments, be practiced utilizing Single Element Detector(s) or can be practiced with Multiple Detector Element Spectrometer System(s) with intensities of a multiplicity of wavelengths being simultaneously monitored by a multiplicity of detector elements therein. As an alternative to the case where multiple element detector(s) are present and one simultaneously obtains data for a plurality of wavelengths at each of the baseline and sample present data acquisition steps, one can utilize single element Detector(s) and sequentially proceed on a wavelength by wavelength basis. The present invention teaches identifying and replacing suspect data at specific wavelengths in a spectroscopic set of data, and said procedure can be repeated until a single data set can be constructed from original and subsequently obtained data, which data set provides good data at all wavelengths, Of course in any recited method of acquiring spectrophotometer intensity ratio data in which the step of providing a spectrophotometer or ellipsometer or the like system can involve orienting the detector system involved to receive electromagnetic radiation which reflects from, or transmits through said sample system.

It is also noted that while the foregoing has related numerous specific examples, variations which vary somewhat from the a specific recited example, or which cut and paste method steps from two of more recited examples should be obvious, or at least strongly suggested, to those skilled in the art. In that light it is also noted that while the foregoing has identified specific approaches to detecting suspect data, it is not necessary that any of said methods be specifically practiced. It is enough that data be identified as suspect, by any method, to practice partial replacement thereof. For instance, ellipsometric PSI and/or DELTA data might be fit very well by a reasonable mathematical model over most of a wavelength range, but not in some small wavelength region within said range. Said deviation from matching might be interpreted to mean that the data acquired in said small wavelength range might be erroneous. It is emphasised that any functional method of detecting bad data in a spectroscopic set of data can be applied in the presently disclosed invention.

Understanding of the present invention will be enhanced by reference to the Detailed Description Section, in conjunction with the Drawings.

SUMMARY OF THE INVENTION

It is therefore a purpose and/or objective of the present invention to teach methodology for identification and replacement of sample system investigation data obtained at at least one wavelength, which data are determined to be of unacceptable precision.

It is another purpose and/or objective of the present invention to, in the practice of spectrophotometry or ellipsometry or the like, teach methodology which enables, in specific examples, determination of whether sample system investigation data is precise or not precise.

It is yet another purpose and/or objective of the present invention to exemplify non-limiting examples of systems which can be used to practice the present invention, said systems each comprising a single source, but variously further comprising single beam or double beam configurations in combination with monochrometer and single element detectors, or in combination with dispersive or filtering elements and multiple detector element containing detector system(s).

It is another purpose and/or objective of the present invention to describe use of spectrophotometer or ellipsometer systems which cause a beam of electromagnetic radiation to approach a reference surface of a sample system at a substantially normal angle, or at an oblique angle of incidence.

Other purposes and/or objectives will become apparent by a reading of the Specification and Claims.

DETAILED DESCRIPTION

The present invention methodology can be practiced utilizing essentially any Source of a Beam of Electromagnetic Radiation (LS), (preferably Spectroscopic), to investigate any Sample System (SS), in combination with any funtionally applicable Detector System(s).

Figure 1:
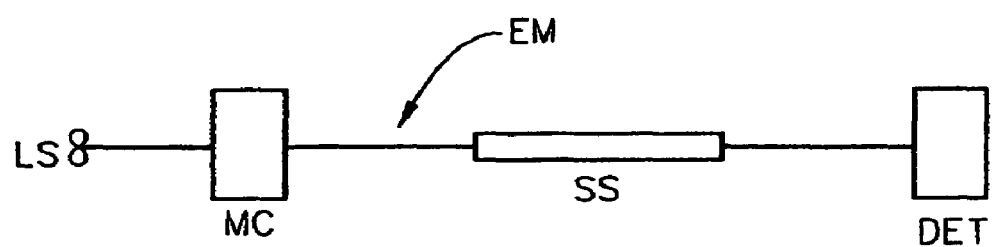
FIG. 1, there is shown one exemplary, non-limiting, system for practicing the present invention methodology, including a monochrometer.
Figure 2:
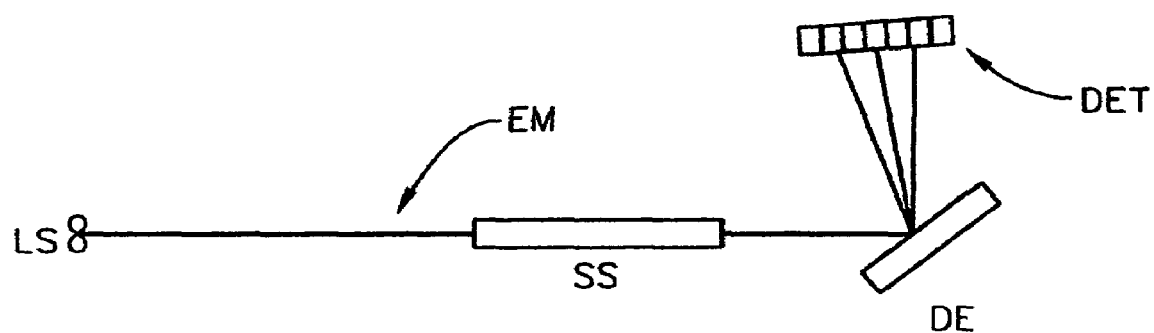
FIG. 2 shows another exemplary system for practicing the present invention methodology, including a dispersive, (or functionally equivalent filtering arrangement), and a multiple detector element detector system.

For instance, FIGS. 1 and 2 indicate Spectrophotometer systems in which an electromagnetic beam (EM) is caused to approach a Sample System (SS) at a shown essentially normal angle of incidence to a reference surface thereof, interact with said Sample System (SS) and then enter a Detector (DET). FIG. 1 further indicates the presence of a Monochrometer (MC) or (MC'), (before or after a sample system), application of which can provide a single wavelength, or sequentially scan through a plurality of Wavelengths. FIG. 2 demonstrates the presence of a Dispersive Element (DE) and a Detector (DET) which comrpises a multiplicity of Detector elements which in use can simultaneously receive a multiplicity of wavelengths. (It is noted that any functionally equivalent means such as a plurality of laterally offset filtering elements can replace the demonstrative dispersive element to provide separated wavelengths to a multi-element Detector, and that any such means of spatially separating wavelengths is to be considered within the terminology "dispersive element" for the purposes of this Specification).

Figure 3:
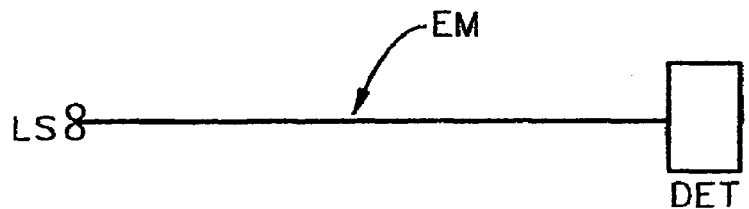
FIG. 3 is demonstrates a "Straight-through" configuration for use in determining baseline data.

FIG. 3 generally demonstates a Spectrophotometer configured in a "Straight-through" configuration. Baseline Data can be obtained from a Spectrophotometer System oriented in such a configuration. It is to be understood that while the straight-through configuration is usually meant to indicate that no sample is present, in this Specification it is generally to be interpreted to also include the case where a standard sample other than open atmosphere is present. That is a standard sample can be present in the path of the electromagentic beam and be within the scope of the terminology "straight-through" as that terminology is used herein.

Figure 4:
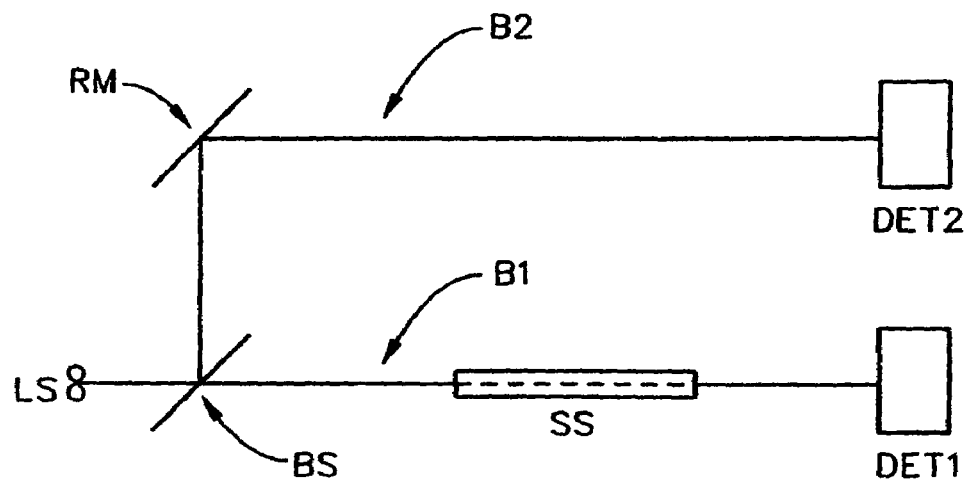
FIG. 4 demonstrates a system which simultaneously provides two beams and two separate detectors.

FIG. 4 demonstrates a Spectrophotometer System wherein a Beam Splitter is applid to form two Beams (B1) and (B2) which are directed to Detectors (DET1) and (DET2) respectively. Beam B1 interacts with a Sample System (SS), while Beam B2 enters Detector (DET2) and represents a Straight-through situation from which a Baseline can be determined. It should be appreciated that this system configuration allows acquiring sample system and baseline data simultaneously. Also note the dashed-line through the Sample System. This is to indicate that said FIG. 4 system is subject to easy re-configuration to provide that Beam (B1) can pass straight-through to Detector (DET1) to allow effective Baseline data to be obtained from Beam (B1). While the system of FIG. 4 provides Source (LS) fluctuations simultaneously to both Detectors (DET1) and (DET2), thereby allowing compensation thereof by forming a ratio of outputs from said Detectors (DET1) and (DET2), however, it must be appreciated that operating parameters of Detectors (DET1) and (DET2) can "float" independent of one another.

Figure 5:
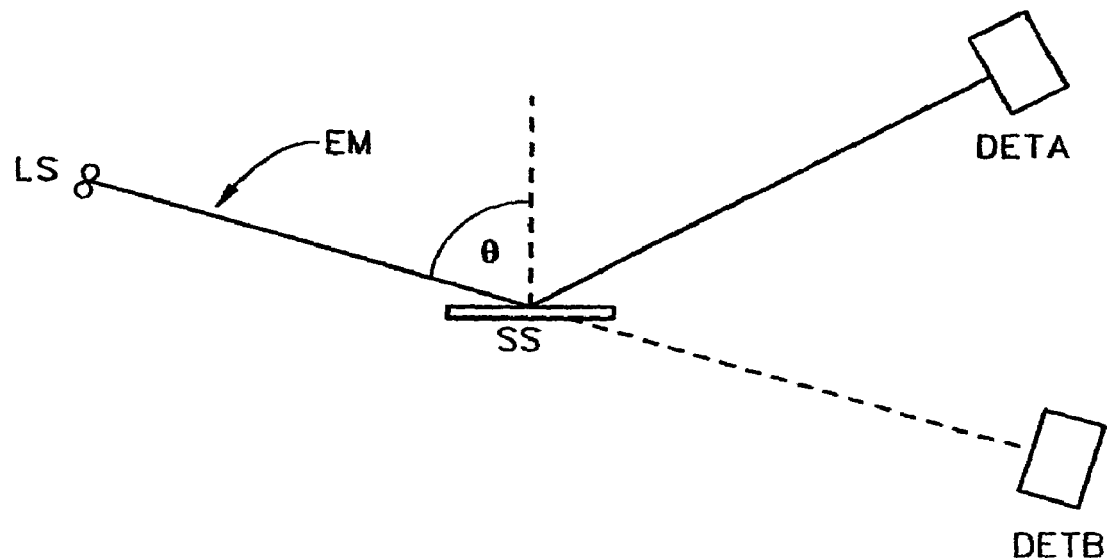
FIG. 5 demonstrates a system for providing a beam of Spectroscopic radiation to a sample system at an oblique angle.

FIG. 5 shows a system for providing a Spectroscopic beam of electromagnetic radiation (EM) to a sample system (SS) at an angle ($\theta$) to a normal to the surface thereof, and further shows that either reflection or tansmission mode data can be obtained via detectors (DETA) and (DETB) respectively. It is noted that the oblique angle of incidence ($\theta$) of the electromagnetic beam can be reduced to 0.0 and make the FIG. 5 system consistant with the configuration of the foregoing Figures.

Figure 6:
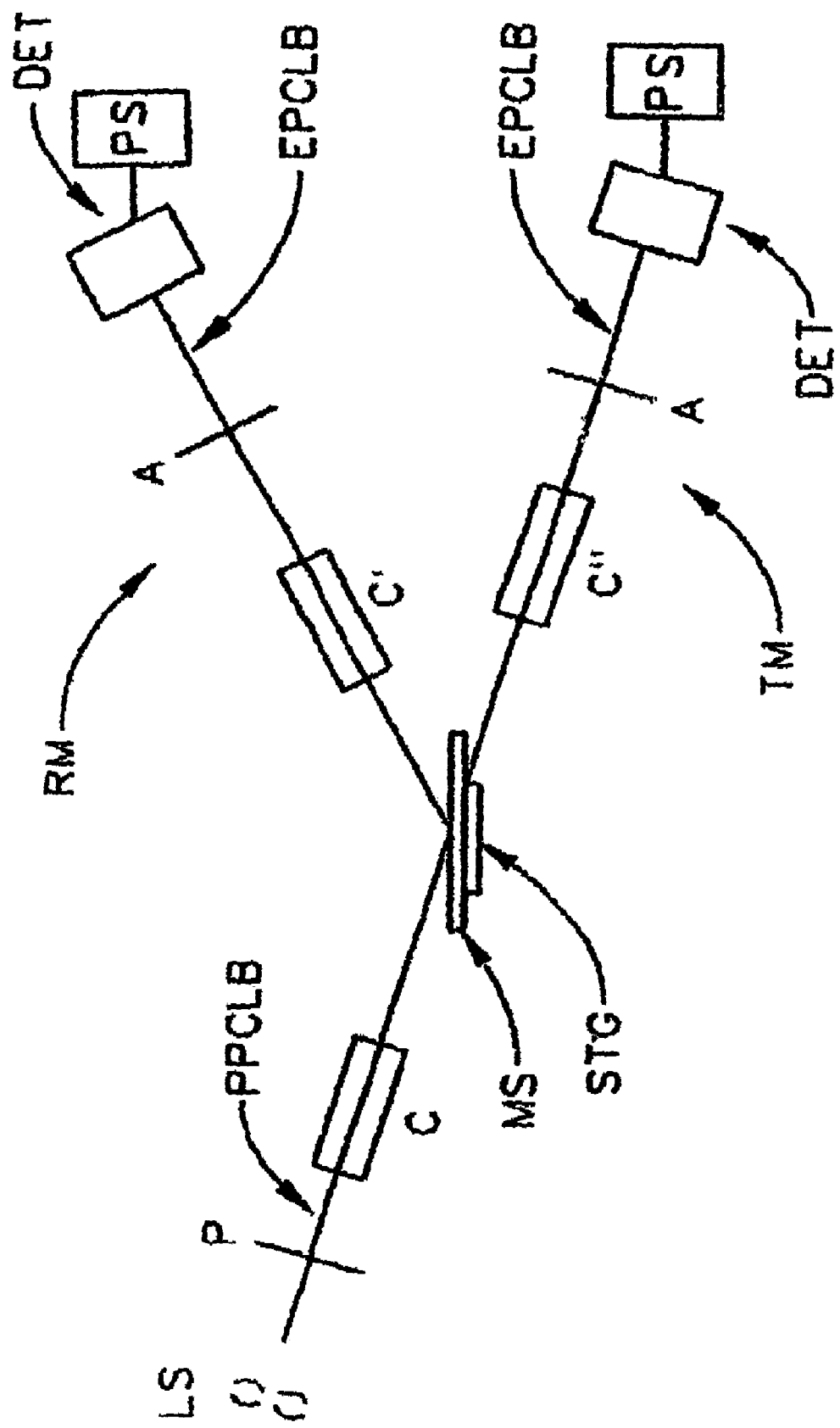
FIG. 6 shows that the system used to collect data can be an ellipsometer or the like system.

It is noted that while not conventional practice, spectrophotometers such as depicted in FIGS. 1–4 can also be applied where the sample system (SS) is reflective of electromagentic radiation, rather than transmissive thereof as indicated. FIGS. 1–4 are therefore to be interpreted in view of FIG. 5, to be encompassing of a configuration wherein electromagnetic radiation refelcts from a Sample System (SS). Further, as indicated by FIG. 6, the system used to collect data can be an ellipsometer. FIG. 6 shows a Source (LS) of a Beam of Spectroscopic Electromagnetic Radiation, a Polarizer (P), a Compensator (C), a Stage (STG) with a Sample (MS) present thereupon, and after sad Sample (MS) there is shown both Reflection (RM) and Transmission (TM) Mode Pathways, each of which comprise a Compensator (C') (C''), Analyzer, Detector DET and Processor System (PS). It is to be understood that the Compensators (C) (C') and (C'') can be deleted and the result is still an Ellipsometer System. The Ellipsometer can be operated in Rotatable or Rotating Polarizer, Rotatable or Rotating Analyzer, Rotatable or Rotating Compensator, which can include two Rotatable or Rotating Compensators. In use of said System a Polarized Beam (PPCLB) of electromagnetic radiation is produced and caused to interact with the Sample (MS). Said interaction changes the Polarization State of said Beam, and said change is quantified by ellipsometric PSI and ellipsometric DELTA, which are determined by detecting Beam (EPCLB). It is alos noted that the Ellipsometer of FIG. 6 can include a Monochromator which is utilzed to scan through a sequency of Wavelengths which are detected by the Detector (DET) one at a time, or a plurality of Wavelengths can be detected smultaneously by use of a Detector (DET) which comprises Dispersive Optics.

It is additionally noted that sample systems investigated by methodology of the present invention can be solids, or can be electromagnetic radiation absorbing analyte containing carrier gas in a flow cell etc. Solid samples can include, for instance, semiconductor substrates which can have various surface layers present thereupon, (eg. $SiO_2$ is demonstrative). With that insight, it is emphasized that the methodology of the preferred embodiment of present invention can be applied to improve the precision repeatability of the results of investigation of any sample system, using any source of monochromatic or spectroscopic electromagnetic radiation, which optionally can be caused to impinge at an oblique or a normal angle to the surface of an investigated sample system.

It again is specifically noted that while single wavelength Sources of Electromagnetic Radiation can be applied in practice of the present invention, preferred Sources of Electromagnetic radiation (LS) provide a spectroscopic range of wavelengths which can be scanned by a monochrometer, or simultaneously monitored.

It is further specifically noted that a spectrometer system is typically considered to include a multi-element detector which simultaneously intercepts a plurality of wavelengths, as opposed to a single-element detector in combination with a monochromator.

In this Specification the terminology "within a selected acceptable range of deviation from", or "within some selected range substantially near" and the like, when used to refer to the value of a ratio formed between the intensities, in relationship to some user determined acceptable value, is to be understood to be user selectable. That is, "deviation from" or "substantially near" can for instance, mean a value selected from a range such as between 0.05% to 10%, with a nominal value of, for instance, 1.5%–2%. The value selected by a user is based in the specific measurements being performed, and the precision thereof required. However, in this Application, any approach to determining that data is suspect is to be considered within the scope of the Claims.

Regardless of how data obtained at one or more wavelengths in a Spectroscopic range of wavelengths is determined to be faulty, the presently disclosed invention provides identification of said faulty data and replacement thereof in a Spectroscopic set of data, rather than reacquiring data over the entire spectroscopic range of wavelengths.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of facilitating production of a good spectroscopic data set comprising the steps of:
   a) acquiring and storing a spectroscopic data set where the independent variable is wavelength, said data set representing the effect a sample has on a beam of electromagnetic radiation over a plurality of wavelengths;
   b) determining that data acquired in step a is not good at at least one, but not at all wavelengths;
   c) reacquiring data at said at least one wavelength and replacing the originally obtained stored data at said at least one wavelength with said reacquired data, such that the necessity of reacquiring an entirely new data set is avoided;

the result being that a stored data set obtained in step a, as modified by data obtained in step c, provides a stored representation of the effect said sample has on said beam of electomagnetic radiation over said plurality of wavelengths.

2. A method as in claim 1, wherein the spectroscopic data set is acquired one wavelength at a time, utilizing a monochromator to scan through said wavelengths.

3. A method as in claim 1 in which a plurality of wavelengths are detected simultaneously.

4. A method as in claim 1 in which the data represents the effect a sample has on reflected intensity.

5. A method as in claim 1 in which the data represents the effect a sample has on transmitted intensity.

6. A method as in claim 1 in which the data represents the effect a sample has on reflected ellipsometric PSI.

7. A method as in claim 1 in which the data represents the effect a sample has on reflected ellipsometric DELTA.

8. A method as in claim 1 in which the data represents the effect a sample has on transmitted ellipsometric PSI.

9. A method as in claim 1 in which the data represents the effect a sample has on transmitted ellipsometric DELTA.

10. A method as in claim 1 in which wavelength is represented by a mathematical equivalent to wavelength.

* * * * *